US012582731B2

(12) United States Patent     (10) Patent No.:   US 12,582,731 B2

Ghatak et al.     (45) Date of Patent:    Mar. 24, 2026

(54) METHOD TO DECONTAMINATE SOLID SURFACE

(71) Applicant: BIOMONETA RESEARCH PVT LTD, Bangalore (IN)

(72) Inventors: Arindam Ghatak, Bangalore (IN); Srividya Janani Venkatraman, Bangalore (IN); Santanu Datta, Bangalore (IN); Sujit Kumar Biswas, Bangalore (IN); Kadambi Sarangapani Ramanujan, Bangalore (IN); Debosmita Kundu, Bangalore (IN); Sujith Raju, Bangalore (IN)

(73) Assignee: BIOMONETA RESEARCH PVT LTD, Bangalore (IN)

( * ) Notice: Subject to any disclaimer, the term of this patent is extended or adjusted under 35 U.S.C. 154(b) by 657 days.

(21) Appl. No.: 17/970,716

(22) Filed: Oct. 21, 2022

(65) Prior Publication Data

US 2023/0390431 A1     Dec. 7, 2023

(51) Int. Cl.

| | |
|---|---|
| *A61L 2/03* | (2006.01) |
| *C11D 1/62* | (2006.01) |
| *C11D 3/48* | (2006.01) |

(52) U.S. Cl.
CPC ..................................... *A61L 2/03* (2013.01); *C11D 1/62* (2013.01); *C11D 3/48* (2013.01)

(58) Field of Classification Search
CPC ..................................... A61L 2/18; A61L 2/03
See application file for complete search history.

(56) References Cited

U.S. PATENT DOCUMENTS

| | | | |
|---|---|---|---|
| 6,258,249 B1 * | 7/2001 | Simpson ................... | A61L 2/03 205/687 |
| 2006/0263238 A1 | 11/2006 | Buhr | |
| 2009/0232748 A1 * | 9/2009 | Capps ................... | A61K 33/34 424/641 |
| 2020/0245616 A1 * | 8/2020 | Lea .......................... | A61L 2/18 |

OTHER PUBLICATIONS

Song, et al.; "Antimicrobial Efficiency and Surface Interactions of Quaternary Ammonium Compound Absorbed on Dielectric Barrier Discharge (DBD) Plasma Treated Fiber-Based Wiping Materials", ACS Applied Materials & Interfaces, ACS Appl. Mater. Interfaces 2020, 12, 298-311.

Salton; "The Adsorption of Cetyltrimethylammonium Bromide by Bacteria, its Action in Releasing Cellular Constituents and its Bactericidal Effects", Department of Colloid Science, University of Cambridge, J. gen, Microbiol. 5, 391-404, 1951.

Ranjan, et al.; "Effects of Electrokinetics and Cationic Surfactant Cetyltrimethylammonium Bromide [CTAB] on the Hydrocarbon Removal and Retention from Contaminated Soils", Environmental Technology, 27:7, 767-776, 2006, DOI: 10.1080/09593332708618686.

* cited by examiner

*Primary Examiner* — Donald R Spamer
(74) *Attorney, Agent, or Firm* — Tarolli, Sundheim, Covell & Tummino LLP

(57)       ABSTRACT

The instant disclosure relates to microbial decontamination of solid surfaces. The disclosure provides method for reducing or eliminating microbes from a solid surface by employing a combination of quaternary ammonium compound coating onto the solid surface and electric field application. Particularly, the method comprises subjecting a solid surface to an electric field comprising a voltage of 2 kV/cm to 6 kV/cm and a capacitance of 0.002 µF to 0.06 µF, to reduce or eliminate the microbes from the solid surface, wherein said solid surface comprises a coating of quaternary ammonium compound. Corresponding products including kit and solid material/device are also provided. The present method has several advantages including but not limiting to high efficiency ($>4$ $\log_{10}$ or $>99.99\%$) in reducing/eliminating microbial load on solid surfaces; requirement of very low concentrations of quaternary ammonium compound [about 0.01% (w/v) to 1% (w/v)] to achieve said high efficiency; and shorter time-periods.

18 Claims, No Drawings

METHOD TO DECONTAMINATE SOLID SURFACE

RELATED APPLICATIONS

The present invention is a U.S. Non-Provisional Applications, claiming priority to Indian Patent Application number 202241032501, filed on Jun. 7, 2022; the entirety of which is hereby incorporated herein by reference.

TECHNICAL FIELD

The instant disclosure is in the field of microbial decontamination, particularly focused towards decontaminating solid surfaces. The disclosure provides method and products for reducing or eliminating microbes from a solid surface by employing combination of quaternary ammonium compound application and specialized electric field application.

BACKGROUND

Various types of solid surfaces/materials (fabric, fibre, metal, wood, plastic, glass, polymer etc.) used today in different industries are subject to contamination by microorganisms (bacteria, virus, fungus, various microbial spores etc.). For instance, various bacteria and viruses are found on different types of surfaces (eg. floors, tables, doorknobs, handles, bed rails, carpets, curtains etc.) in health care facilities, food production facilities, schools and the community in general.

In medical/health care industry, microbes get trapped on the solid surfaces (mattress, chair cushion, instruments/devices etc.) which are difficult to eliminate by washing. Particularly, surfaces such as a mattress in hospital, chair cushions in public places get exposed to a variety of microorganisms, which are often drug-resistant. Often these microorganisms get impregnated inside the crevices, created due to the nature of the fabric used. Also, aprons and PPEs, specifically those worn in laboratories and hospitals, are to be either disposed or cleaned thoroughly. These are rarely soiled or greasy and making these clothing products microbe-free is a key requirement. Additionally, high touch wood or metal surfaces such as tables and chairs contain a high microbial load, which often transmits individual skin bacteria to another person.

Likewise, in the large food processing industry and large industrial kitchens, it is often necessary to have cleaned solid surfaces to make cutting and chopping surfaces microbe-free as these surfaces become rapidly contaminated. Various types of solid surfaces are used today in the food industry, such as plastic, stainless steel, glass and wood which are subject to contamination by microorganisms responsible for the cross-contamination of food by contact with working surfaces.

The contamination of solid surfaces can be a serious public health problem, and in fact some disease outbreaks can be linked to contamination of solid surfaces. The risk of infection resulting from transmission through contaminated solid surfaces depends on a number of factors, such as the level of shedding of infective particles, their stability on the solid surfaces and resistance to decontamination procedures, and the low dose required for infection. In fact, many microorganisms such as bacteria and viruses, stay infectious for up to several weeks which is considered another important factor in environmental transmission.

Cleaning and disinfection procedures using antimicrobial agents are the common techniques employed for reducing microbial load on solid surfaces. However, the effectiveness of said techniques is limited as the microbial reduction levels achieved are not as desired. Additionally, said techniques suffer from other drawbacks such as the need for very high concentrations/amounts of antimicrobial agents, very long exposure times especially for high microbial load/highly contaminated surfaces, use of hazardous chemicals for decontamination, and use of manual decontamination processes which are error-prone. Therefore, effective methods for reducing or eliminating microbial contamination on solid surfaces is an urgent need of the art. The present disclosure addresses said need.

SUMMARY

The present disclosure relates to a method of reducing or eliminating microbes from a solid surface comprising subjecting the solid surface to an electric field comprising a voltage of 2 kilovolts/cm (kV/cm) to 6 kilovolts/cm (kV/cm) and a capacitance of 0.002 microfarads (μF) to 0.06 microfarads (μF), to reduce or eliminate the microbes from the solid surface, wherein the solid surface comprises a coating of quaternary ammonium compound.

In embodiments of the present disclosure, the method of reducing or eliminating microbes from a solid surface comprises:

providing a solid surface, wherein the solid surface is pre-coated with a quaternary ammonium compound to obtain a coated solid surface, or coating the solid surface with a quaternary ammonium compound to obtain a coated solid surface; and subjecting the coated solid surface to the electric field comprising the voltage of 2 kilovolts/cm (kV/cm) to 6 kilovolts/cm (kV/cm) and the capacitance of 0.002 microfarads (μF) to 0.06 microfarads (μF), to reduce or eliminate the microbes from the solid surface.

In embodiments of the present method, the quaternary ammonium compound (QAC) is a quaternary ammonium salt (QAS).

In embodiments of the present method, the quaternary ammonium salt (QAS) is a cetrimonium salt or a steartrimonium salt.

In embodiments of the present method, the cetrimonium salt or the steartrimonium salt is selected from a group comprising cetyltrimethylammonium bromide (CTAB), cetyltrimethylammonium chloride (CTAC), stearyl trimethyl ammonium chloride (STAC) and mixtures thereof.

In embodiments of the present method, the quaternary ammonium salt is CTAB.

In embodiments of the present method, the coated solid surface is subjected to electric field comprising a voltage of 2 kV/cm to 4 kV/cm and a capacitance of 0.0025 μF to 0.05 μF.

In embodiments of the present method, the solid surface is selected from a group comprising fabric, fibre, metal, wood, plastic, glass, polymer, and combinations thereof.

The present disclosure further provides a kit comprising:

a quaternary ammonium compound, or a solid material coated with the quaternary ammonium compound;

an electrical power source to supply an electric field comprising a voltage of 2 kV/cm to 6 kV/cm and a capacitance of 0.002 μF to 0.06 μF; and an instruction manual comprising instructions for reducing or eliminating microbes from a solid surface.

The present disclosure also provides a solid material or a device comprising:

a coating of quaternary ammonium compound; and a means for an electrical power source to supply an electric field comprising a voltage of 2 kV/cm to 6 kV/cm and a capacitance of 0.002 µF to 0.06 µF.

DESCRIPTION

In view of the limitations discussed above, the present disclosure aims at addressing the need for methods to reduce or eliminate microbes on solid surfaces.

Particularly, an objective of the present disclosure is to provide a method for effective microbial kill on solid surfaces contaminated with microbes by activation/potentiation of said solid surfaces.

Another objective of the present disclosure is to achieve reduction or elimination of microbes from solid surfaces at very low concentrations of antimicrobial agent(s), thereby making the approach safe/non-toxic to humans.

Yet another objective of the present disclosure is to achieve reduction or elimination of microbes from solid surfaces in a very short time period.

Still another objective of the present disclosure is to achieve up to 100% reduction or elimination of microbes from solid surfaces in a very short time period.

Still another objective of the present disclosure is to achieve the ability to destroy a broad spectrum of microbes with very high efficiency, including Gram-positive bacteria, Gram-negative bacteria, viruses, fungi, spores, etc.

Accordingly, the present disclosure intends to provide a simple, economical, effective, environment friendly and sustainable solution for simultaneously addressing the aforesaid need and to meet the aforesaid objectives.

Before going into greater detail, provided below are definitions of some terms used throughout the present disclosure.

As used in the present disclosure, the term "solid surface" refers to any portion/part of a solid material including a flexible solid material or a non-flexible/hard solid material. Few examples of solid materials include but are not limited to fabric, fibre, metal, wood, plastic, glass and polymer. A person skilled in the art will understand that solid surface according to the present disclosure is any portion of a solid material which has a possibility or risk of microbial contamination. In some embodiments, the solid surface includes the surface (outer layer or exposed portion) of a solid material. In some embodiments, the solid surface includes inner portion (excluding the outer layer/exposed portion) of the solid material. For instance, in case of fabric, the solid surface encompasses surface or outer exposed layer of the fabric, or the inner threads used to manufacture the fabric.

As used in the present disclosure, the term/phrase "coated solid surface" refers to a solid surface which is already coated (i.e. pre-coated) with quaternary ammonium compound, or a solid surface wherein quaternary ammonium compound is actively coated onto it by any coating step/procedure.

As used in the present disclosure, the terms "reducing or eliminating microbes", "microbial kill", "reducing microbial load" or "eliminating microbial load" are used interchangeably and refer to decontamination or inactivation or killing of microbes. Based on the present disclosure, a person skilled in the art will understand said feature to mean microbial decontamination of any solid surface.

Method for Reducing or Eliminating Microbes from a Solid Surface

The present disclosure provides a method for reducing or eliminating microbes from a solid surface by employing a combination of antimicrobial agent treatment and electric field application on to said solid surface.

Particularly, the present disclosure provides a method for reducing or eliminating microbes from a solid surface comprising subjecting said solid surface to an electric field comprising a voltage of 2 kilovolts/cm (kV/cm) to 6 kilovolts/cm (kV/cm) and a capacitance of 0.002 microfarads (µF) to 0.06 microfarads (µF), to reduce or eliminate the microbes from the solid surface, wherein the solid surface comprises a coating of quaternary ammonium compound.

In some embodiments, the method comprises:

providing a solid surface, wherein said solid surface is pre-coated with a quaternary ammonium compound to obtain a coated solid surface; and subjecting the coated solid surface to the electric field comprising the voltage of 2 kilovolts/cm (kV/cm) to 6 kilovolts/cm (kV/cm) and the capacitance of 0.002 microfarads (µF) to 0.06 microfarads (µF), to reduce or eliminate the microbes from the solid surface.

In some embodiments, the method comprises:

coating the solid surface with a quaternary ammonium compound to obtain a coated solid surface; and subjecting the coated solid surface to the electric field comprising the voltage of 2 kilovolts/cm (kV/cm) to 6 kilovolts/cm (kV/cm) and the capacitance of 0.002 microfarads (µF) to 0.06 microfarads (µF), to reduce or eliminate the microbes from the solid surface.

In some embodiments, solid surface comprising the coating of quaternary ammonium compound is subjected to the electric field after contamination with the microbes.

In some embodiments, coating the solid surface with a quaternary ammonium compound is carried out at a temperature of about 25° C. to 100° C. for a time period of about 2 hours to 10 hours.

In some embodiments, the quaternary ammonium compound (QAC) is a quaternary ammonium salt (QAS).

In some embodiments, the quaternary ammonium salt (QAS) comprises a quaternary ammonium cation and a halide anion. In some embodiments, the halide is bromide, chloride, fluoride or iodide.

In some embodiments, the quaternary ammonium salt (QAS) is an alkyl quaternary ammonium salt.

In some embodiments, the quaternary ammonium salt (QAS) is a linear alkyl quaternary ammonium salt or a branched alkyl quaternary ammonium salt.

In some embodiments, the quaternary ammonium salt (QAS) is a linear alkyl quaternary ammonium salt having aliphatic carbon chain length of C8 to C22, or a branched alkyl quaternary ammonium salt having an aliphatic carbon chain length of C8 to C22.

In some embodiments, the quaternary ammonium salt (QAS) is a linear alkyl quaternary ammonium salt having aliphatic carbon chain length of C8 to C22.

In some embodiments, the quaternary ammonium salt (QAS) is a linear alkyl quaternary ammonium salt having aliphatic carbon chain length selected from C8, C9, C10, C11, C12, C13, C14, C15, C16, C17, C18, C19, C20, C21 and C22.

In some embodiments, the quaternary ammonium compound (QAC) or the quaternary ammonium salt (QAS) is a linear alkyl quaternary ammonium salt having aliphatic carbon chain length of C16 to C18.

In some embodiments, the quaternary ammonium compound (QAC) or the quaternary ammonium salt (QAS) is a linear alkyl quaternary ammonium salt having aliphatic carbon chain length of C16 to C20.

In some embodiments, the linear alkyl quaternary ammonium salt having aliphatic carbon chain length between C8 to C22 is a cetrimonium salt or a steartrimonium salt.

In some embodiments, the linear alkyl quaternary ammonium salt having aliphatic carbon chain length of C8 to C22 is selected from cetyltrimethylammonium bromide (CTAB), cetyltrimethylammonium chloride (CTAC), cetyltrimethylammonium fluoride (CTAF), cetyltrimethylammonium iodide (CTAI), stearyl trimethyl ammonium chloride (STAC), stearyl trimethyl ammonium bromide (STAB), stearyl trimethyl ammonium fluoride (STAF), stearyl trimethyl ammonium iodide (STAI), or mixtures thereof.

In some embodiments, the QAC or the QAS is a linear alkyl quaternary ammonium salt having aliphatic carbon chain length of C16 to C18 selected from CTAB, CTAC, CTAF, CTAI, STAC, STAB, STAF, STAI, or mixtures thereof.

In some embodiments, the linear alkyl quaternary ammonium salt having aliphatic carbon chain length of C8 to C22 is CTAB. In some embodiments, the linear alkyl quaternary ammonium salt having aliphatic carbon chain length of C16 to C18 is CTAB.

In some embodiments, the QAC or the QAS is a linear alkyl quaternary ammonium salt having aliphatic carbon chain length of C16 which is CTAB, CTAC, CTAF, CTAI, or mixtures thereof.

In some embodiments, the QAC or the QAS is a linear alkyl quaternary ammonium salt having aliphatic carbon chain length of C18 which is STAC, STAB, STAF, STAI, or mixtures thereof.

In some embodiments, the QAC or the QAS is CTAB.

In some embodiments, the solid surface is coated with the quaternary ammonium compound (QAC), wherein the QAC is at a concentration of about 0.01% (w/v) to 1% (w/v), including all values and ranges therefrom.

In some embodiments, the solid surface is coated with a linear alkyl quaternary ammonium salt having aliphatic carbon chain length of C8 to C22 at a concentration of about 0.01% (w/v) to 1% (w/v), including all values and ranges therefrom.

In some embodiments, the solid surface is coated with a linear alkyl quaternary ammonium salt having aliphatic carbon chain length of C16 to C18 at a concentration of about 0.01% (w/v) to 1% (w/v), including all values and ranges therefrom.

In some embodiments, the solid surface is coated with CTAB at a concentration of about 0.01% (w/v) to 1% (w/v), including all values and ranges therefrom.

In some embodiments, the solid surface is coated with the quaternary ammonium compound (QAC) at a concentration of about 0.01% (w/v) to 0.75% (w/v).

In some embodiments, the solid surface is coated with a linear alkyl quaternary ammonium salt having aliphatic carbon chain length of C8 to C22 at a concentration of about 0.01% (w/v) to 0.75% (w/v), including all values and ranges therefrom.

In some embodiments, the solid surface is coated with a linear alkyl quaternary ammonium salt having aliphatic carbon chain length of C16 to C18 at a concentration of about 0.01% (w/v) to 0.75% (w/v), including all values and ranges therefrom.

In some embodiments, the solid surface is coated with CTAB at a concentration of about 0.01% (w/v) to 0.75% (w/v).

In some embodiments, the solid surface is coated with the quaternary ammonium compound (QAC) at a concentration of about 0.01% (w/v), about 0.05% (w/v), about (w/v), about 0.25% (w/v), about 0.50% (w/v), or about 0.75% (w/v).

In some embodiments, the solid surface is coated with linear alkyl quaternary ammonium salt having aliphatic carbon chain length of C8 to C22 at a concentration of about 0.01% (w/v), about 0.05% (w/v), about 0.1% (w/v), about 0.25% (w/v), about (w/v), or about 0.75% (w/v).

In some embodiments, the solid surface is coated with linear alkyl quaternary ammonium salt having aliphatic carbon chain length of C16 to C18 at a concentration of about 0.01% (w/v), about 0.05% (w/v), about 0.1% (w/v), about 0.25% (w/v), about (w/v), or about 0.75% (w/v).

In some embodiments, the solid surface is coated with CTAB at a concentration of about 0.01% (w/v), about 0.05% (w/v), about 0.1% (w/v), about 0.25% (w/v), about (w/v), or about 0.75% (w/v).

In some embodiments, the solid surface is coated with about 0.01 to 0.5 milligram (mg) of the quaternary ammonium compound (QAC) per square centimeter (cm$^2$) of said solid surface.

In some embodiments, the solid surface is coated with a linear alkyl quaternary ammonium salt having aliphatic carbon chain length of C16 to C18 at about 0.01 to 0.5 mg/cm$^2$ of said solid surface, including all values and ranges therefrom.

In some embodiments, the solid surface is coated with CTAB at about 0.01 to 0.5 mg/cm$^2$ of said solid surface, including all values and ranges therefrom.

In some embodiments, the solid surface is coated with quaternary ammonium compound (QAC) at about 0.01 to 0.05 mg/cm$^2$ of said solid surface, including all values and ranges therefrom.

In some embodiments, the coating of the quaternary ammonium compound (QAC) on the solid surface has a thickness of about 0.1 to 3 millimeter (mm), including all values and ranges therefrom.

In some embodiments, the coating of the linear alkyl quaternary ammonium salt having aliphatic carbon chain length of C16 to C18 on the solid surface has a thickness of about 0.1 to 3 mm, including all values and ranges therefrom.

In some embodiments, the CTAB coat on the solid surface has a thickness of about to 3 mm, including all values and ranges therefrom.

In some embodiments, the CTAB coat on the solid surface has a thickness of about to 0.5 mm, including all values and ranges therefrom.

In some embodiments, the coated solid surface is subjected to electric field comprising a voltage of 2 kilovolts/cm (kV/cm) to 6 kilovolts/cm (kV/cm) and a capacitance of 0.0025 μF to 0.05 μF, including all values and ranges therefrom.

In some embodiments, the coated solid surface is subjected to electric field comprising a voltage of 2 kilovolts/cm (kV/cm) to 4 kilovolts/cm (kV/cm) and a capacitance of 0.002 μF to 0.06 μF, including all values and ranges therefrom.

In some embodiments, the coated solid surface is subjected to electric field comprising a voltage of 2 kilovolts/cm (kV/cm) to 4 kilovolts/cm (kV/cm) and a capacitance of 0.0025 μF to 0.05 μF, including all values and ranges therefrom.

In some embodiments, the coated solid surface is subjected to electric field comprising a voltage of 2 kilovolts/cm (kV/cm) to 3 kilovolts/cm (kV/cm) and a capacitance of 0.0025 µF to 0.05 µF, including all values and ranges therefrom.

In some embodiments, the electric field is provided by electrical power source selected from a group comprising direct current (DC) power source, alternating current (AC) power source, switch mode power supply (SMPS) source, or pulsed power source.

In some embodiments, the electric field is provided by SMPS source.

In some embodiments, the coated solid surface is subjected to electric field for a time-period of about 3 minutes to 90 minutes.

In some embodiments, the coated solid surface is subjected to electric field for a time-period of about 3 minutes to 10 minutes.

In some embodiments, the coated solid surface is subjected to electric field for a time-period of about 4 minutes to 10 minutes.

In some embodiments, the coated solid surface is subjected to electric field for a time-period of about 4 minutes to 20 minutes.

In some embodiments, the coated solid surface is subjected to electric field for a time-period of about 4 minutes to 30 minutes.

In some embodiments, the coated solid surface is subjected to electric field for a time-period of about 4 minutes to 60 minutes.

In some embodiments, the coated solid surface is subjected to electric field for a time-period of about 10 minutes to 60 minutes.

In some embodiments, the coated solid surface is subjected to electric field for a time-period of about 4 minutes, 5 minutes, 10 minutes, 20 minutes, 30 minutes, 45 minutes, 60 minutes, or 90 minutes.

In some embodiments, the solid surface is a conducting material or a non-conducting material.

In some embodiments, the solid surface is selected from a group comprising fabric, fibre, metal, wood, plastic, glass, polymer, and combinations thereof.

In some embodiments, the solid surface is any fabric or fibre material known in the art which is susceptible to microbial contamination. In some embodiments, the solid surface is a fabric selected from a group comprising cotton, polyester, nylon, other woven fabrics and combinations thereof.

In some embodiments, the solid surface is any metal surface known in the art which is susceptible to microbial contamination. In some embodiments, the solid surface is a metal selected from a group comprising aluminium, stainless steel, miled steel, copper and combinations thereof.

In some embodiments, the solid surface is any wood surface known in the art which is susceptible to microbial contamination. In some embodiments, the solid surface is any plastic surface known in the art which is susceptible to microbial contamination. In some embodiments, the solid surface is any glass surface known in the art which is susceptible to microbial contamination. In some embodiments, the solid surface is any polymer surface known in the art which is susceptible to microbial contamination.

In some embodiments, the microbes are selected from a group comprising bacteria, virus, fungus, bacterial spores, fungal spores and combinations thereof.

In some embodiments, the microbe is a bacteria selected from a group comprising Cocci, Bacilli, Vibrios, Spirilla, spirochaetes and combinations thereof.

In some embodiments, the microbe is a virus selected from a group comprising single-stranded DNA (ssDNA) virus, double-stranded DNA (dsDNA) virus, single-stranded RNA (ssRNA) virus, double-stranded RNA (dsRNA) virus and combinations thereof.

In some embodiments, the microbe is a fungus selected from a group comprising Basidiomycota, Ascomycota, Glomeromycota, Microsporidia, Blastocladiomycota, Neocallimastigomycota, Chytridiomycota and combinations thereof.

In some embodiments, the microbe is a microbial spore selected from a group comprising bacterial spore, fungal spore or a combination thereof.

In some embodiments, the present method achieves a microbial load reduction on the solid surface by a minimum of 4 $\log_{10}$. In some embodiments, the present method achieves a microbial load reduction on the solid surface by about 4 $\log_{10}$ to 7 $\log_{10}$. In some embodiments, the present method achieves a microbial load reduction of >4 $\log_{10}$. In some embodiments, the present method achieves a microbial load reduction of >5 $\log_{10}$. In some embodiments, the present method achieves a microbial load reduction of >6 $\log_{10}$. In some embodiments, the present method achieves a microbial load reduction of >7 $\log_{10}$.

In some embodiments, the present method achieves a microbial load reduction of >4 $\log_{10}$, wherein the electric field is applied for about 3 minutes to about 4 minutes.

In some embodiments, the present method reduces microbial load on the solid surface or decontaminates the solid surface by at least about 95%. In some embodiments, the present method reduces microbial load on the solid surface or decontaminates the solid surface by about 95% to greater than 99.99%, including all values and ranges therefrom.

In some embodiments, the present method reduces microbial load on the solid surface or decontaminates the solid surface by about 95%, 95.5%, 96%, 96.5%, 97%, 97.5%, 98%, 98.5%, 99%, 99.5%, or >99.9999%. In some embodiments, the present method eliminates or kills up to 100% microbes present on the solid surface, or decontaminates up to 100% of the solid surface.

In some embodiments, the present method eliminates or kills >99.99% microbes present on the solid surface, wherein the electric field is applied for about 3 minutes to about 4 minutes.

In some embodiments, the method of reducing or eliminating microbes from a solid surface comprises:

providing a solid surface, wherein the solid surface is pre-coated with a quaternary ammonium compound to obtain a coated solid surface, or coating a solid surface with a quaternary ammonium compound to obtain a coated solid surface, wherein the solid surface is a fabric, fibre, metal, wood, plastic, glass or polymer, and the quaternary ammonium compound is a linear alkyl quaternary ammonium salt having aliphatic carbon chain length of C8 to C22; and subjecting the coated solid surface to the electric field comprising the voltage of about 2 kilovolts/cm (kV/cm) to 6 kilovolts/cm (kV/cm) and the capacitance of about 0.002 µF to 0.06 µF, to reduce or eliminate the microbes from the solid surface.

In some embodiments, the method of reducing or eliminating microbes from a solid surface comprises:

providing a solid surface, wherein the solid surface is pre-coated with a quaternary ammonium compound to obtain a coated solid surface, or coating a solid surface with a quaternary ammonium compound to obtain a coated solid surface, wherein the solid surface is a fabric, fibre, metal, wood, plastic, glass or polymer, and the quaternary ammonium compound is a cetrimonium salt or a steartrimonium salt; and subjecting the coated solid surface to the electric field comprising the voltage of about 2 kilovolts/cm (kV/cm) to 6 kilovolts/cm (kV/cm) and the capacitance of about 0.002 µF to 0.06 µF, to reduce or eliminate the microbes from the solid surface.

In some embodiments, the method of reducing or eliminating microbes from a solid surface comprises:

providing a solid surface, wherein the solid surface is pre-coated with a quaternary ammonium compound to obtain a coated solid surface, or coating a solid surface with a quaternary ammonium compound to obtain a coated solid surface, wherein the solid surface is a fabric, fibre, metal, wood, plastic, glass or polymer, and the quaternary ammonium compound is CTAB; and subjecting the coated solid surface to the electric field comprising the voltage of about 2 kilovolts/cm (kV/cm) to 6 kilovolts/cm (kV/cm) and the capacitance of about 0.002 µF to 0.06 µF, to reduce or eliminate the microbes from the solid surface.

In some embodiments, the method of reducing or eliminating microbes from a solid surface comprises:

providing a solid surface, wherein the solid surface is pre-coated with a quaternary ammonium compound to obtain a coated solid surface, wherein the solid surface is a fabric, fibre, metal, wood, plastic, glass or polymer, and the quaternary ammonium compound is CTAB; and subjecting the coated solid surface to the electric field for a time-period of about 4 minutes to 90 minutes, said electric field comprising the voltage of about 2 kilovolts/cm (kV/cm) to 6 kilovolts/cm (kV/cm) and the capacitance of about 0.002 µF to 0.06 µF, to reduce or eliminate the microbes from the solid surface, wherein the method achieves a microbial load reduction of about 4 $\log_{10}$ to 7 $\log_{10}$, or the method reduces microbial load on the solid surface by about 95% to 99.9999%.

In some embodiments, the method of reducing or eliminating microbes from a solid surface comprises:

providing a solid surface, wherein the solid surface is pre-coated with a quaternary ammonium compound to obtain a coated solid surface, wherein the solid surface is a fabric, fibre, metal, wood, plastic, glass or polymer, and the quaternary ammonium compound is CTAB; and subjecting the coated solid surface to the electric field for a time-period of about 4 minutes to 60 minutes, said electric field comprising the voltage of about 2 kilovolts/cm (kV/cm) to 4 kilovolts/cm (kV/cm) and the capacitance of about 0.0025 µF to 0.05 µF, to reduce or eliminate the microbes from the solid surface, wherein the method achieves a microbial load reduction of about 4 $\log_{10}$ to 7 $\log_{10}$, or the method reduces or eliminates the microbes from the solid surface by about 98% to 99.9999%.

In some embodiments, the method of reducing or eliminating microbes from a solid surface comprises:

providing a solid surface, wherein the solid surface is pre-coated with a quaternary ammonium compound to obtain a coated solid surface, wherein the solid surface is a fabric, and the quaternary ammonium compound is CTAB; and subjecting the coated solid surface to the electric field for a time-period of about 4 minutes to 90 minutes, said electric field comprising the voltage of about 2 kilovolts/cm (kV/cm) to 4 kilovolts/cm (kV/cm) and the capacitance of about 0.0025 µF to 0.05 µF, to reduce or eliminate the microbes from the solid surface, wherein the method achieves a microbial load reduction of about 4 $\log_{10}$ to 7 $\log_{10}$, or the method reduces or eliminates the microbes from the solid surface by about 95% to 99.9999%.

In some embodiments, the method of reducing or eliminating microbes from a solid surface comprises:

providing a solid surface, wherein the solid surface is pre-coated with a quaternary ammonium compound to obtain a coated solid surface, wherein the solid surface is a metal, and the quaternary ammonium compound is CTAB; and subjecting the coated solid surface to the electric field for a time-period of about 4 minutes to 90 minutes, said electric field comprising the voltage of about 2 kilovolts/cm (kV/cm) to 4 kilovolts/cm (kV/cm) and the capacitance of about 0.0025 µF to 0.05 µF, to reduce or eliminate the microbes from the solid surface, wherein the method achieves a microbial load reduction of about 4 $\log_{10}$ to 7 $\log_{10}$, or the method reduces or eliminates the microbes from the solid surface by about 95% to 99.9999%.

In some embodiments, the method of reducing or eliminating microbes from a solid surface comprises:

providing a solid surface, wherein the solid surface is pre-coated with a quaternary ammonium compound to obtain a coated solid surface, wherein the solid surface is a polymer, and the quaternary ammonium compound is CTAB; and subjecting the coated solid surface to the electric field for a time-period of about 4 minutes to 90 minutes, said electric field comprising the voltage of about 2 kilovolts/cm (kV/cm) to 4 kilovolts/cm (kV/cm) and the capacitance of about 0.0025 µF to 0.05 µF, to reduce or eliminate the microbes from the solid surface, wherein the method achieves a microbial load reduction of about 4 $\log_{10}$ to 7 $\log_{10}$, or the method reduces or eliminates the microbes from the solid surface by about 95% to 99.9999%.

In some embodiments, the method of reducing or eliminating microbes from a solid surface comprises:

coating a solid surface with a quaternary ammonium compound at a temperature of about 25° C. to 100° C. for a time period of about 2 hours to 10 hours, to obtain a coated solid surface, wherein the solid surface is a fabric, metal, wood, glass or polymer, and the quaternary ammonium compound is a linear alkyl quaternary ammonium salt having aliphatic carbon chain length of C8 to C22; and subjecting the coated solid surface to the electric field for a time-period of about 4 minutes to 60 minutes, said electric field comprising the voltage of about 2 kilovolts/cm (kV/cm) to 4 kilovolts/cm (kV/cm) and the capacitance of about 0.0025 µF to 0.05 µF, to reduce or eliminate the microbes from the solid surface, wherein the method achieves a microbial load reduction of about 4 $\log_{10}$ to 7 $\log_{10}$, or the method reduces or eliminates the microbes from the solid surface by about 95% to 99.9999%.

In some embodiments, the method of reducing or eliminating microbes from a solid surface comprises:

coating a solid surface with a quaternary ammonium compound at a temperature of about 25° C. to 100° C. for a time period of about 2 hours to 10 hours, to obtain a coated solid surface, wherein the solid surface is a fabric, metal, wood, glass or polymer, and the quaternary ammonium compound is a cetrimonium salt or a steatrimonium salt; and subjecting the coated solid surface to the electric field for a time-period of about 4 minutes to 60 minutes, said electric field comprising the voltage of about 2 kilovolts/cm (kV/cm) to 4 kilovolts/cm (kV/cm) and the capacitance of about 0.0025 μF to 0.05 μF, to reduce or eliminate the microbes from the solid surface, wherein the method achieves a microbial load reduction of about 4 $\log_{10}$ to 7 $\log_{10}$, or the method reduces or eliminates the microbes from the solid surface by about 95% to 99.9999%.

In some embodiments, the method of reducing or eliminating microbes from a solid surface comprises:

coating a solid surface with a quaternary ammonium compound at a temperature of about 80° C. for a time period of about 10 hours, to obtain a coated solid surface, wherein the solid surface is a fabric, metal, wood, glass or polymer, and the quaternary ammonium compound is CTAB; and subjecting the coated solid surface to the electric field for a time-period of about 4 minutes to 60 minutes, said electric field comprising the voltage of about 2 kilovolts/cm (kV/cm) to 4 kilovolts/cm (kV/cm) and the capacitance of about 0.0025 μF to 0.05 μF, to reduce or eliminate the microbes from the solid surface, wherein the method achieves a microbial load reduction of about 4 $\log_{10}$ to 7 $\log_{10}$, or the method reduces or eliminates the microbes from the solid surface by about 95% to 99.9999%.

Accordingly, the present method resulting in decontamination of solid surface employs a combined approach of coating the solid surface with quaternary ammonium compound followed by applying specialized electric field to achieve significant reduction or elimination of microbes from said solid surface. Particularly, the method potentiates/activates the solid surface coated with quaternary ammonium compound (eg. a linear alkyl quaternary ammonium salt having aliphatic carbon chain length between C8 to C22 or a cetrimonium salt such as CTAB) in the presence of the electric field wherein, the activated solid surface gains the ability to destroy a broad spectrum of microbes with very high efficiency, including Gram-positive bacteria, Gram-negative bacteria, viruses, fungal species, spores, etc. The present method of significantly enhancing microbial kill on solid surfaces using electric field permits such a kill in minutes at very low quaternary ammonium compound concentrations.

Particularly, the combined application of electric field and quaternary ammonium compound (eg. a linear alkyl quaternary ammonium salt having aliphatic carbon chain length between C8 to C22 such as CTAB) act synergistically in the present method to inactivate/kill microbes. Without wishing to be bound by any theory, the inventors propose the following mechanism for said synergistic effect:

Quaternary ammonium compounds such as linear alkyl quaternary ammonium salts having aliphatic carbon chain length between C16 to C18 or cetrimonium salts (eg. CTAB) are membrane-active agents which inactivate microbes by targeting their cytoplasmic membrane, but first, they must breach the outer cell wall. When quaternary ammonium compound such as cetrimonium salts (eg. CTAB) are coated on a solid surface, the long flexible chain help the molecules to orient themselves and puncture holes on microbe cellular envelop. However, this orientation is random in nature and thus, the effective time to eliminate a higher load of microorganisms take longer period. When said quaternary ammonium compound coated solid surfaces are subjected to an exposure of electric field with specific parameters (voltage and capacitance) as described herein, the orientation of these long chains are in tandem and thus time to inactivate a higher load of microbes is less. The electric field increases the trans-membrane voltage of the microbial cell above its resting value, leading to an electric current that presumably flows through these pores as they form the path of least resistance. This current flow may be analogous to the electroporation of bacteria in which the pores formed in the cell wall are stabilized. The intracellular components then leak from the pores. This process leads to irreversible destruction of the cells. Therefore, the solid surface coated with antimicrobial compound (quaternary ammonium compound) coupled with electric field displays an enhanced electro-chemical microbicidal action compared to what they would have achieved separately.

Further, the present method of decontaminating 'solid surface' with high efficiency (up to >99.99% elimination of microbes) is a long standing need of prior art. Said method which is particularly applicable to microbes present/trapped on to 'solid surfaces' is not comparable with microbial decontamination of other sources (eg. air, water etc.). This is because of the following non-limiting reasons:

Air and water, being fluid, do not have crevices where microbes can reside and remain infectious for a long period of time. Thus, reaching crevices is one of the biggest challenges in solid surface decontamination.

Solid surfaces have to be treated in situ or on the site. On the other hand, air and water can be channeled to a treatment location such as an Heating Ventilation and Air Conditioning (HVAC) duct or water purification equipment/container/pit.

Methods for air/water decontamination are primarily continuous methods, whereas, the existing/prior art methods for solid surfaces are often discontinuous/staggered thereby making the decontamination process extremely challenging. Methods for air/water decontamination also do not employ manual intervention, whereas the existing/prior art methods to decontaminate solid surfaces involve manual intervention.

Methods to decontaminate air/water often involve multiple technological interventions. For example, using filter+UV+Ionization (for air) and using RO+UF Filtration+UV (for water). On the other hand, for solid surfaces, the commonly used method is to clean/wipe with a generic detergent (eg. 70% ethanol, chlorohexidine etc.) which may not result in efficient elimination of microorganisms.

Advantages

The present method of reducing or eliminating microbes from a solid surface as described herein have several advantages including but not limiting to:

significantly better efficiency (up to >99.99%) in reducing or eliminating microbial load on the solid surface.

combination of quaternary ammonium compound and electric field application as described herein is more efficient in removing trapped microbes, which otherwise cannot be removed by washing or conventional disinfection procedures.

use of very low concentration (about 0.01% to 1%) of quaternary ammonium compound, thereby making the method safe/non-toxic to humans but yet achieving significantly improved efficiency by removing/eliminating microbes from solid surface up to 100%.

achieving significantly improved efficiency by reducing/eliminating microbes from solid surface by up to 100% within short time-periods (about 4 minutes to 90 minutes).

Kit

The present disclosure further provides a kit comprising:

a quaternary ammonium compound, or a solid material coated with the quaternary ammonium compound;

an electrical power source to supply an electric field comprising a voltage of 2 kilovolts/cm (kV/cm) to 6 kilovolts/cm (kV/cm) and a capacitance of 0.002 μF to 0.06 μF; and an instruction manual comprising instructions for reducing or eliminating microbes from a solid surface.

In some embodiments, the quaternary ammonium compound (QAC) is coated onto surface of the solid material.

In some embodiments, the quaternary ammonium compound (QAC) is a quaternary ammonium salt.

In some embodiments, the quaternary ammonium salt (QAS) comprises a quaternary ammonium cation and a halide anion. In some embodiments, the halide is bromide, chloride, fluoride or iodide.

In some embodiments, the quaternary ammonium salt (QAS) is an alkyl quaternary ammonium salt. In some embodiments, the quaternary ammonium salt (QAS) is a linear alkyl quaternary ammonium salt or a branched alkyl quaternary ammonium salt.

In some embodiments, the quaternary ammonium salt (QAS) is a linear alkyl quaternary ammonium salt having aliphatic carbon chain length of C8 to C22, or a branched alkyl quaternary ammonium salt having an aliphatic carbon chain length of C8 to C22.

In some embodiments, the quaternary ammonium salt (QAS) is a linear alkyl quaternary ammonium salt having aliphatic carbon chain length of C8 to C22. In some embodiments, the quaternary ammonium salt (QAS) is a linear alkyl quaternary ammonium salt having aliphatic carbon chain length selected from C8, C9, C10, C11, C12, C13, C14, C15, C16, C17, C18, C19, C20, C21 and C22.

In some embodiments, the quaternary ammonium compound (QAC) or the quaternary ammonium salt (QAS) is a linear alkyl quaternary ammonium salt having aliphatic carbon chain length of C16 to C18.

In some embodiments, the quaternary ammonium compound (QAC) or the quaternary ammonium salt (QAS) is a linear alkyl quaternary ammonium salt having aliphatic carbon chain length of C16 to C20.

In some embodiments, the linear alkyl quaternary ammonium salt having aliphatic carbon chain length between C8 to C22 is a cetrimonium salt or a steartrimonium salt.

In some embodiments, the linear alkyl quaternary ammonium salt having aliphatic carbon chain length of C8 to C22 is selected from cetyltrimethylammonium bromide (CTAB), cetyltrimethylammonium chloride (CTAC), cetyltrimethylammonium fluoride (CTAF), cetyltrimethylammonium iodide (CTAI), stearyl trimethyl ammonium chloride (STAC), stearyl trimethyl ammonium bromide (STAB), stearyl trimethyl ammonium fluoride (STAF), stearyl trimethyl ammonium iodide (STAI), or mixtures thereof.

In some embodiments, the QAC or the QAS is a linear alkyl quaternary ammonium salt having aliphatic carbon chain length of C16 to C18 selected from CTAB, CTAC, CTAF, CTAI, STAC, STAB, STAF, STAI, or mixtures thereof.

In some embodiments, the linear alkyl quaternary ammonium salt having aliphatic carbon chain length of C8 to C22 is CTAB. In some embodiments, the linear alkyl quaternary ammonium salt having aliphatic carbon chain length of C16 to C18 is CTAB.

In some embodiments, the QAC or the QAS is a linear alkyl quaternary ammonium salt having aliphatic carbon chain length of C16 which is CTAB, CTAC, CTAF, CTAI, or mixtures thereof.

In some embodiments, the QAC or the QAS is a linear alkyl quaternary ammonium salt having aliphatic carbon chain length of C18 which is STAC, STAB, STAF, STAI, or mixtures thereof.

In some embodiments, the QAC or the QAS is CTAB.

In some embodiments, the quaternary ammonium compound (QAC) in the kit is at a concentration of about 0.01% (w/v) to 1% (w/v).

In some embodiments, the linear alkyl quaternary ammonium salt having aliphatic carbon chain length of C8 to C22 in the kit is at a concentration of about 0.01% (w/v) to 1% (w/v).

In some embodiments, the linear alkyl quaternary ammonium salt having aliphatic carbon chain length of C16 to C18 in the kit is at a concentration of about 0.01% (w/v) to 1% (w/v).

In some embodiments, the CTAB in the kit is at a concentration of about 0.01% (w/v) to 1% (w/v).

In some embodiments, the surface of the solid material is coated with about 0.01% (w/v) to 1% (w/v) of the quaternary ammonium compound.

In some embodiments, the surface of the solid material is coated with about 0.01% (w/v) to 1% (w/v) of a linear alkyl quaternary ammonium salt having aliphatic carbon chain length of C8 to C22.

In some embodiments, the surface of the solid material is coated with about 0.01% (w/v) to 1% (w/v) of a linear alkyl quaternary ammonium salt having aliphatic carbon chain length of C16 to C18.

In some embodiments, the surface of the solid material is coated with about 0.01% (w/v) to 1% (w/v) of CTAB.

In some embodiments, the surface of the solid material is coated with about 0.01 to 0.5 mg of the quaternary ammonium compound per cm$^2$ of said surface.

In some embodiments, the surface of the solid material is coated with a linear alkyl quaternary ammonium salt having aliphatic carbon chain length of C8 to C22 at about 0.01 to 0.5 mg/cm$^2$ of said surface.

In some embodiments, the surface of the solid material is coated with a linear alkyl quaternary ammonium salt having aliphatic carbon chain length of C16 to C18 at about 0.01 to 0.5 mg/cm$^2$ of said surface.

In some embodiments, the surface of the solid material is coated with CTAB at about 0.01 to 0.5 mg/cm$^2$ of said surface.

In some embodiments, the coating of the quaternary ammonium compound on the solid material has a thickness of about 0.1 to 3 mm.

In some embodiments, the coating of the linear alkyl quaternary ammonium salt having aliphatic carbon chain length of C8 to C22 on the solid material has a thickness of about 0.1 to 3 mm.

In some embodiments, the coating of the linear alkyl quaternary ammonium salt having aliphatic carbon chain length of C16 to C18 on the solid material has a thickness of about 0.1 to 3 mm.

In some embodiments, the CTAB coat on the solid material has a thickness of about 0.1 to 3 mm.

In some embodiments, the electrical power source supplies an electric field comprising a voltage of 2 kilovolts/cm (kV/cm) to 4 kilovolts/cm (kV/cm) and a capacitance of 0.0025 µF to 0.05 µF.

In some embodiments, the kit comprises:

a quaternary ammonium compound, or a solid material coated with the quaternary ammonium compound;

an electrical power source to supply an electric field comprising a voltage of 2 kilovolts/cm (kV/cm) to 4 kilovolts/cm (kV/cm) and a capacitance of 0.0025 µF to 0.05 µF; and an instruction manual comprising instructions for reducing or eliminating microbes from a solid surface.

In some embodiments, the kit comprises:

cetrimonium salt, or a solid material coated with the linear alkyl quaternary ammonium salt having aliphatic carbon chain length of C8 to C22;

an electrical power source to supply an electric field comprising a voltage of 2 kilovolts/cm (kV/cm) to 4 kilovolts/cm (kV/cm) and a capacitance of 0.0025 µF to 0.05 µF; and an instruction manual comprising instructions for reducing or eliminating microbes from a solid surface.

In some embodiments, the kit comprises:

CTAB, or a solid material coated with the CTAB;

an electrical power source to supply an electric field comprising a voltage of 2 kilovolts/cm (kV/cm) to 4 kilovolts/cm (kV/cm) and a capacitance of 0.0025 µF to 0.05 µF; and an instruction manual comprising instructions for reducing or eliminating microbes from a solid surface.

In all embodiments of the kit provided herein, the additional features of the quaternary ammonium compound and electric field is as described by any of the embodiments mentioned above for method of reducing or eliminating microbes from a solid surface. For the sake of brevity, and avoiding repetition, each of those embodiments are not being reiterated here again. However, each of the said embodiments, completely fall within the purview of the kit.

In some embodiments, the solid material in the kit is selected from but not limited to medical device/equipment or industrial device/equipment. In some embodiments, the solid material is selected from chairs in medical clinics and hospitals, mattresses, bed linen, personal protective equipment (PPE), curtains, any other medical or industrial device/equipment and combinations thereof.

Device

The present disclosure also provides a solid material or a device comprising:

a coating of quaternary ammonium compound (QAC); and a means for an electrical power source to supply an electric field comprising a voltage of 2 kilovolts/cm (kV/cm) to 6 kilovolts/cm (kV/cm) and a capacitance of 0.002 µF to 0.06 µF.

In some embodiments, the quaternary ammonium compound (QAC) is coated onto surface of the solid material or device.

In some embodiments, the quaternary ammonium compound (QAC) is a quaternary ammonium salt.

In some embodiments, the quaternary ammonium salt (QAS) comprises a quaternary ammonium cation and a halide anion. In some embodiments, the halide is bromide, chloride, fluoride or iodide.

In some embodiments, the quaternary ammonium salt (QAS) is an alkyl quaternary ammonium salt. In some embodiments, the quaternary ammonium salt (QAS) is a linear alkyl quaternary ammonium salt or a branched alkyl quaternary ammonium salt.

In some embodiments, the quaternary ammonium salt (QAS) is a linear alkyl quaternary ammonium salt having aliphatic carbon chain length of C8 to C22, or a branched alkyl quaternary ammonium salt having an aliphatic carbon chain length of C8 to C22.

In some embodiments, the quaternary ammonium salt (QAS) is a linear alkyl quaternary ammonium salt having aliphatic carbon chain length of C8 to C22. In some embodiments, the quaternary ammonium salt (QAS) is a linear alkyl quaternary ammonium salt having aliphatic carbon chain length selected from C8, C9, C10, C11, C12, C13, C14, C15, C16, C17, C18, C19, C20, C21 and C22.

In some embodiments, the quaternary ammonium compound (QAC) or the quaternary ammonium salt (QAS) is a linear alkyl quaternary ammonium salt having aliphatic carbon chain length of C16 to C18.

In some embodiments, the linear alkyl quaternary ammonium salt having aliphatic carbon chain length between C8 to C22 is a cetrimonium salt or a steartrimonium salt.

In some embodiments, the linear alkyl quaternary ammonium salt having aliphatic carbon chain length of C8 to C22 is selected from cetyltrimethylammonium bromide (CTAB), cetyltrimethylammonium chloride (CTAC), cetyltrimethylammonium fluoride (CTAF), cetyltrimethylammonium iodide (CTAI), stearyl trimethyl ammonium chloride (STAC), stearyl trimethyl ammonium bromide (STAB), stearyl trimethyl ammonium fluoride (STAF), stearyl trimethyl ammonium iodide (STAI), or mixtures thereof.

In some embodiments, the QAC or the QAS is a linear alkyl quaternary ammonium salt having aliphatic carbon chain length of C16 to C18 selected from CTAB, CTAC, CTAF, CTAI, STAC, STAB, STAF, STAI, or mixtures thereof.

In some embodiments, the linear alkyl quaternary ammonium salt having aliphatic carbon chain length of C8 to C22 is CTAB. In some embodiments, the linear alkyl quaternary ammonium salt having aliphatic carbon chain length of C16 to C18 is CTAB.

In some embodiments, the QAC or the QAS is a linear alkyl quaternary ammonium salt having aliphatic carbon chain length of C16 which is CTAB, CTAC, CTAF, CTAI, or mixtures thereof.

In some embodiments, the QAC or the QAS is a linear alkyl quaternary ammonium salt having aliphatic carbon chain length of C18 which is STAC, STAB, STAF, STAI, or mixtures thereof.

In some embodiments, the QAC or the QAS is CTAB.

In some embodiments, the quaternary ammonium compound (QAC) in the kit is at a concentration of about 0.01% (w/v) to 1% (w/v).

In some embodiments, the linear alkyl quaternary ammonium salt having aliphatic carbon chain length of C8 to C22 coated on the solid material or device is at a concentration of about 0.01% (w/v) to 1% (w/v).

In some embodiments, the linear alkyl quaternary ammonium salt having aliphatic carbon chain length of C16 to C18 coated on the solid material or device is at a concentration of about 0.01% (w/v) to 1% (w/v).

In some embodiments, the CTAB coated on the solid material or device is at a concentration of about 0.01% (w/v) to 1% (w/v).

In some embodiments, the surface of the solid material or device is coated with about 0.01% (w/v) to 1% (w/v) of the quaternary ammonium compound.

In some embodiments, the surface of the solid material or device is coated with about 0.01% (w/v) to 1% (w/v) of the linear alkyl quaternary ammonium salt having aliphatic carbon chain length of C8 to C22.

In some embodiments, the surface of the solid material or device is coated with about 0.01% (w/v) to 1% (w/v) of CTAB.

In some embodiments, the surface of the solid material or device is coated with about 0.01 to 0.5 mg of the quaternary ammonium compound per $cm^2$ of said surface.

In some embodiments, the surface of the solid material or device is coated with linear alkyl quaternary ammonium salt having aliphatic carbon chain length of C8 to C22 at about 0.01 to 0.5 mg/$cm^2$ of said surface.

In some embodiments, the surface of the solid material or device is coated with CTAB at about 0.01 to 0.5 mg/$cm^2$ of said surface.

In some embodiments, the coating of the quaternary ammonium compound on the solid material or device has a thickness of about 0.1 to 3 mm.

In some embodiments, the coating of the linear alkyl quaternary ammonium salt having aliphatic carbon chain length of C8 to C22 on the solid material or device has a thickness of about 0.1 to 3 mm.

In some embodiments, the CTAB coat on the solid material or device has a thickness of about 0.1 to 3 mm.

In some embodiments, the electrical power source supplies an electric field comprising a voltage of 2 kilovolts/cm (kV/cm) to 4 kilovolts/cm (kV/cm) and a capacitance of 0.0025 µF to 0.05 µF.

In some embodiments, the solid material or the device comprises:
- a coating of quaternary ammonium compound; and
- a means for an electrical power source to supply an electric field comprising a voltage of 2 kilovolts/cm (kV/cm) to 4 kilovolts/cm (kV/cm) and a capacitance of 0.0025 µF to 0.05 µF.

In some embodiments, the solid material or the device comprises:
- a coating of a linear alkyl quaternary ammonium salt having aliphatic carbon chain length of C8 to C22; and
- a means for an electrical power source to supply an electric field comprising a voltage of 2 kilovolts/cm (kV/cm) to 4 kilovolts/cm (kV/cm) and a capacitance of 0.0025 µF to 0.05 µF.

In some embodiments, the solid material or the device comprises:
- a coating of a linear alkyl quaternary ammonium salt having aliphatic carbon chain length of C16 to C18; and
- a means for an electrical power source to supply an electric field comprising a voltage of 2 kilovolts/cm (kV/cm) to 4 kilovolts/cm (kV/cm) and a capacitance of 0.0025 µF to 0.05 µF.

In some embodiments, the solid material or the device comprises:
- a coating of CTAB; and
- a means for an electrical power source to supply an electric field comprising a voltage of 2 kilovolts/cm (kV/cm) to 4 kilovolts/cm (kV/cm) and a capacitance of 0.0025 µF to 0.05 µF.

In all embodiments of the solid material or device provided herein, the additional features of the quaternary ammonium compound and electric field is as described by any of the embodiments mentioned above for method of reducing or eliminating microbes from a solid surface. For the sake of brevity, and avoiding repetition, each of those embodiments are not being reiterated here again. However, each of the said embodiments, completely fall within the purview of the solid material or device.

In some embodiments, the solid material in the kit is selected from but not limited to medical device/equipment or industrial device/equipment. In some embodiments, the solid material is selected from chairs in medical clinics and hospitals, mattresses, bed linen, personal protective equipment (PPE), curtains, any other medical or industrial device/equipment and combinations thereof.

Applications of the Method, Kit and Solid Material/Device

As discussed above, efficient decontamination/elimination of microbes present or trapped on solid surfaces is a continuing need in all industries. The present method and products can be employed on solid materials/surfaces including but not limiting to those used in health care/medical, food production/processing facilities, public places and community in general. A person skilled in the art will understand that the present method can be employed on any solid surface having a risk of microbial contamination. Particularly, the method and products can be employed on all types of flexible and non-flexible/hard solid materials or surfaces which require microbial decontamination, for instance, high touch metal/fabric/wood/glass/polymer based solid surfaces like table, mattress, aprons, PPEs, chair cushion, cutting and chopping surfaces, etc. Said applications and examples of solid surfaces are not limiting and a person skilled in the art will understand that the method and products of the present disclosure are applicable in any industry or community in general employing solid materials/surfaces requiring microbial decontamination.

Additional embodiments and features of the present disclosure will be apparent to one of ordinary skill in art based upon description provided herein. The embodiments herein provide various features and advantageous details thereof in the description. Descriptions of well-known/conventional methods and techniques are omitted so as to not unnecessarily obscure the embodiments herein. Further, the disclosure herein provides for examples illustrating the above described embodiments, and in order to illustrate the embodiments of the present disclosure certain aspects have been employed. The examples used herein for such illustration are intended merely to facilitate an understanding of ways in which the embodiments herein may be practiced and to further enable those of skill in the art to practice the embodiments herein. Accordingly, the following examples should not be construed as limiting the scope of the embodiments herein.

EXAMPLES

Example 1

Microbial Decontamination of Solid Surface Coated with Quaternary Ammonium Compound The following process was employed to prepare solid surfaces coated with different quaternary ammonium compounds (QACs):

The solid surface (cotton cloth) was suspended in a solution containing cetyltrimethylammonium bromide (CTAB) or alkyl dimethyl benzyl ammonium chloride (benzalkonium chloride) at various concentrations for about 2 hours. The solid surfaces were then heat dried in a furnace where the temperature was set at about 80° C., for about 8 hours. Once dried, the solid surfaces coated with QAC were ready to be used for various applications.

The microbial load reduction on the solid surfaces coated with quaternary ammonium compound alone are shown in Table 1.

TABLE 1

| Experiment | Microbial Load Reduction (Log$_{10}$ Scale) | | | | | |
| | 0 mins | 10 mins | 30 mins | 45 mins | 60 mins | 90 mins |
| --- | --- | --- | --- | --- | --- | --- |
| Cotton Cloth coated with 0.01% w/v of CTAB | 0.00 | 1.11 | 2.52 | 4.35 | 7.60 | 7.60 |
| Cotton Cloth coated with 0.05% w/v of CTAB | 0.00 | 1.18 | 2.54 | 5.12 | 7.32 | 7.32 |
| Cotton Cloth coated with 0.1% w/v of CTAB | 0.00 | 7.41 | 7.41 | 7.41 | 7.41 | 7.41 |
| Cotton Cloth coated with 0.25% w/v of CTAB | 0.00 | 7.45 | 7.45 | 7.45 | 7.45 | 7.45 |
| Cotton Cloth coated with 0.5% w/v of CTAB | 0.00 | 7.00 | 7.00 | 7.00 | 7.00 | 7.00 |
| Cotton Cloth coated with 0.75% w/v of CTAB | 0.00 | 7.78 | 7.78 | 7.78 | 7.78 | 7.78 |
| Cotton Cloth coated with 10% w/v benzalkonium chloride | 0.00 | 0.92 | 3.10 | 7.30 | 7.30 | 7.30 |
| Cotton Cloth coated with 1% w/v benzalkonium chloride | 0.00 | 0.82 | 1.70 | 4.57 | 7.48 | 7.48 |

As seen from Table 1, cotton clothes coated with QACs were subjected to microbial load. Reduction in microbial load was analysed at different concentrations of QACs. It was observed that a linear alkyl quaternary ammonium salt having aliphatic carbon chain length of C8 to C22 such as a cetrimonium salt (CTAB) at low concentrations (0.01% w/v, 0.05% w/v, 0.1% w/v, 0.25% w/v, 0.5% w/v and 0.75% w/v) showed significantly high elimination of the subjected microbial load (>7 log$_{10}$ or >99.99999%) starting from 10 minutes.

Example 2

Microbial Decontamination of Flexible Solid Surface by Employing Quaternary Ammonium Compound Coating and Electric Field Application The effect of QAC coating and electric field application on flexible solid surfaces was analysed. The solid surface analysed was fabric (cotton cloth). The procedure for coating of QAC (CTAB or benzalkonium chloride) onto the cotton cloth was identical to the procedure described in Example 1. The final coated amount of QAC (CTAB or benzalkonium chloride) was between 0.01-0.05 mg/cm² of the solid surface. The electric field in this experiment was applied via. switch mode power supply (SMPS) with a voltage of 4 kV/cm coupled with a capacitance of 0.05 μF for various time-periods. The results on microbial load changes are shown in Table 2.

TABLE 2

| Sl. No. | Method | Microbial Load Reduction (Log$_{10}$ Scale) | | |
| | | 0 mins | 10 mins | 30 mins |
| --- | --- | --- | --- | --- |
| Experiment 1: Cotton cloth coated with QAC (0.01% w/v CTAB) | Trial 1: Without Electric Field | 0.00 | 1.06 | 2.15 |
| | Trial 2: With Electric Field | 0.00 | 7.30 | 7.30 |
| | Trial 3: Without Electric Field | 0.00 | 1.09 | 2.16 |
| | Trial 4: With Electric Field | 0.00 | 7.48 | 7.48 |
| Experiment 2: Cotton cloth coated with 10% w/v benzalkonium chloride | Without Electric Field | 0.00 | 0.92 | 3.10 |
| | With Electric Field | 0.00 | 1.16 | 3.03 |
| Experiment 3: Cotton cloth coated with 1% w/v benzalkonium chloride | Without Electric Field | 0.00 | 0.82 | 1.70 |
| | With Electric Field | 0.00 | 1.51 | 2.39 |
| Experiment 4: Cotton cloth | Trial 1: Cotton cloth | 0.00 | 0.10 | 0.28 |
| | Trial 2: Cotton cloth + Electric Field | 0.00 | 1.22 | 1.40 |

As seen from Table 2, flexible solid surfaces (cotton cloth) were subjected to microbial load. Reduction in microbial load was analysed using different methods.

It was observed that when the cotton cloth was coated with very low concentration of cetrimonium salt (CTAB) followed by application of electric field, the subjected microbial load was completely eliminated (>7 log$_{10}$ reduction in microbial load or >99.99999% reduction in microbial load) within 10 minutes [see Experiment 1—Trial 2 and Trial 4]. On the other hand, when cotton cloth coated with CTAB was not subjected to electric field application, there was no significant reduction in the microbial load until 30 minutes [see results of Experiment 1—Trial 1 and Trial 3 showing a significantly low log$_{10}$ reduction of ≤2.16]. Further, under normal conditions, when the cotton cloth alone was left undisturbed [see Experiment 4—Trial 1], the microbial load remained largely unaltered; and when the cotton cloth was subjected to electric field application only [see Experiment 4—Trial 2], no significant microbial load reduction was observed.

The above results indicate the synergy of combining the steps of coating quaternary ammonium compound (eg. linear alkyl quaternary ammonium salts having aliphatic carbon chain length between C8 to C22 such as CTAB) followed by electric field application to achieve >7 log$_{10}$ reduction or >99.99999% reduction/elimination of microbes from solid surfaces within a very short time span.

Example 3

Microbial Decontamination of Hard Solid Surface by Employing Quaternary Ammonium Compound Coating and Electric Field Application The effect of QAC coating and electric field application on non-flexible/hard solid surfaces was analysed. The solid surface analysed was a metal surface (aluminium plate). The coating procedure of QAC (cetrimonium salt—CTAB) was identical to the procedure described in Example 1. The final coated amount of CTAB was between 0.01-0.05 mg/cm² of the solid surface. The electric field in this experiment was applied via. switch mode power supply (SMPS) with a voltage of 4 kV/cm coupled with a capacitance of 0.05 μF for various time-periods. The results of microbial load changes are shown in Table 3.

TABLE 3

| Experiment No. | Method | Microbial Load Reduction (Log$_{10}$ Scale) | | | | |
| | | 0 mins | 5 mins | 10 mins | 20 mins | 30 mins |
|---|---|---|---|---|---|---|
| 1 | Metal alone | 0.00 | 0.11 | 0.66 | 0.73 | 0.77 |
| 2 | Metal + Electric Field | 0.00 | 3.26 | 4.64 | 7.34 | 7.34 |
| 3 | Metal + QAC (0.01% w/v CTAB) | 0.00 | 0.22 | 0.42 | 0.57 | 0.95 |
| 4 | Metal + QAC (0.01% w/v CTAB) + Electric Field [Present Invention] | 0.00 | 5.55 | 7.51 | 7.51 | 7.51 |

As seen from Table 3, hard solid surfaces (aluminium plate) loaded with microorganisms were analysed for microbial load reduction using different methods. It was observed that when the metal was coated with low concentration of cetrimonium salt (CTAB) followed by application of electric field, the subjected microbial load was completely eliminated (>7 log$_{10}$ reduction in microbial load or >99.99999% reduction in microbial load) within 10 minutes [Experiment No. 4]. On the other hand, when the metal was coated with CTAB alone, there was no significant reduction in the microbial load even at 30 minutes [Experiment No. 3]. Further, when the metal was subjected to electric field application alone, the microbial load was significantly reduced (>7 log$_{10}$ reduction in microbial load or >99.99999% reduction in microbial load) only at around 20 minutes [Experiment No. 2]. Lastly, under normal conditions, when the metal was left undisturbed, the microbial load remained largely unaltered over a period of 30 minutes [Experiment No. 1].

The above results again indicate a complete electrochemical elimination of microorganisms when QAC (eg. linear alkyl quaternary ammonium salts having aliphatic carbon chain length between C8 to C22 such as CTAB) at sub-lethal concentration combined with an electric field was employed. Particularly, the results demonstrate a synergy of combining steps of quaternary ammonium compound application and electric field application to achieve >7 log$_{10}$ or >99.99999% reduction/elimination of microbes from solid surfaces within a very short time-period.

Example 4

Microbial Decontamination of Solid Surface by Employing Quaternary Ammonium Compound Coating and Varying Electric Fields The effect of QAC coating and varying electric field application on solid surfaces was analysed. The solid surface analysed was polyester cotton fabric in the ratio 90:10. The procedure for coating of QAC (CTAB) onto the said polyester cotton fabric was identical to the procedure described in Example 1. The CTAB concentration employed was 0.02±0.005% w/v and the final coated amount of QAC (CTAB) was between 0.01-0.05 mg/cm$^2$ of the solid surface. The electric field in this experiment was applied via. switch mode power supply (SMPS). Said electric field had a voltage of 4 kV/cm DC and the capacitance was varied between 0.05 μF to 0.000025 μF. The results of microbial load changes at various time-periods are shown in Table 4.

TABLE 4

| Experiment No. | Capacitance | Microbial load reduction (Log$_{10}$ scale) | | |
| | | 3 mins | 4 mins | 5 mins |
|---|---|---|---|---|
| 1 | 0.05 μF | 4.44 | 6.78 | 6.78 |
| 2 | 0.025 μF | 4.32 | 6.78 | 6.78 |
| 3 | 0.0025 μF | 2.12 | 3.27 | 6.78 |
| 4 | 0.00025 μF | 1.01 | 3.20 | 4.44 |
| 5 | 0.000025 μF | 1.01 | 2.09 | 3.20 |

As seen from Table 4, when the solid surface was coated with cetrimonium salt (CTAB) followed by application of electric field at different capacitance values (between μF to 0.05 μF), the subjected microbial load was eliminated (>6 log$_{10}$ reduction in microbial load or >99.9999% reduction in microbial load) within 4 to 5 minutes [see Experiments 1 to 3]. On the other hand, when the solid surface was coated with CTAB followed by application of electric field at capacitance values beyond 0.0025 μF (i.e. 0.00025 μF or 0.000025 μF), a notable reduction in the microbial load was observed only around 5 minutes [see Experiments 4 and 5].

Another set of experiments were conducted wherein the procedure for coating of QAC (CTAB) onto the polyester cotton fabric was identical to the procedure described in Example 1. The CTAB concentration employed was 0.02±0.005% w/v and the final coated amount of QAC (CTAB) was between 0.01-0.05 mg/cm$^2$ of the solid surface. The electric field in this experiment was applied via. switch mode power supply (SMPS). Said electric field had a capacitance of 0.05 μF and the voltage was varied between 0.5 kV/cm to 3 kV/cm. The results of microbial load changes at 10 minutes are shown in Table 5.

TABLE 5

| Experiment No. | Applied Voltage (kilo volts/cm) | Microbial load reduction (Log$_{10}$ scale) at 10 mins |
|---|---|---|
| 1 | 0.5 | 1.18 |
| 2 | 0.75 | 1.22 |
| 3 | 1 | 1.44 |
| 4 | 1.25 | 1.68 |
| 5 | 2 | 7.68 |
| 6 | 2.5 | 8.78 |
| 7 | 3 | 9.42 |

As seen from Table 5, when the solid surface was coated with cetrimonium salt (CTAB) followed by application of electric field at different voltage values –2 kV/cm, 2.5 kV/cm and 3 kV/cm, the subjected microbial load was eliminated (>7 log$_{10}$ reduction in microbial load or >99.99999% reduction in microbial load) within 10 minutes [see Experiments 5 to 7]. Similar efficiency (microbial load reduction) was observed when the electric field having voltage until 6 kV/cm was employed according to the present method. On the other hand, when the solid surface was coated with CTAB followed by application of electric field at voltage values lower than 2 kV/cm (0.5 kV/cm, 0.75 kV/cm, 1 kV/cm or 1.25 kV/cm), there was no notable reduction in the microbial load [see Experiments 1 and 4].

The above results indicate the synergistic combination of quaternary ammonium compound application (eg. linear alkyl quaternary ammonium salts having aliphatic carbon chain length between C8 to C22 including cetrimonium salts such as CTAB) coupled with specialized electric field application comprising a capacitance between 0.002 µF to 0.06 µF and a voltage between 2 kV/cm to 6 kV/cm to achieve complete reduction/elimination of microbes from solid surfaces within a very short time span.

The foregoing description of the specific embodiments reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments in this disclosure have been described in terms of preferred embodiments, those skilled in the art will recognize that the embodiments herein can be practiced with modification within the spirit and scope of the embodiments as described herein.

Throughout this specification, the word "comprise", or variations such as "comprises" or "comprising" or "including" wherever used, will be understood to imply the inclusion of a stated element, integer or step, or group of elements, integers or steps, but not the exclusion of any other element, integer or step, or group of elements, integers or steps.

Throughout this specification, the term 'combinations thereof' or 'any combination thereof' or 'any combinations thereof' are used interchangeably and are intended to have the same meaning, as regularly known in the field of patents disclosures.

As used herein, the term "comprising" when placed before the recitation of steps in a method means that the method encompasses one or more steps that are additional to those expressly recited, and that the additional one or more steps may be performed before, between, and/or after the recited steps. For example, a method comprising steps a, b, and c encompasses a method of steps a, b, x, and c, a method of steps a, b, c, and x, as well as a method of steps x, a, b, and c. Furthermore, the term "comprising" when placed before the recitation of steps in a method does not (although it may) require sequential performance of the listed steps, unless the content clearly dictates otherwise. For example, a method comprising steps a, b, and c encompasses, for example, a method of performing steps in the order of steps a, c, and b, the order of steps c, b, and a, and the order of steps c, a, and b, etc.

As used in this specification and the appended claims, the singular forms "a," "an" and "the" includes both singular and plural references unless the content clearly dictates otherwise. For example, the term "inserted at a position" as used herein in reference to a polypeptide sequence refers to insertion at one or more (such as one, two, three, etc.) amino acid positions in the polypeptide sequence. The use of the expression 'at least' or 'at least one' suggests the use of one or more elements or ingredients or quantities, as the use may be in the embodiment of the disclosure to achieve one or more of the desired objects or results. As such, the terms "a" (or "an"), "one or more", and "at least one" can be used interchangeably herein.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The suffix "(s)" at the end of any term in the present disclosure envisages in scope both the singular and plural forms of said term.

Numerical ranges stated in the form 'from x to y' include the values mentioned and those values that lie within the range of the respective measurement accuracy as known to the skilled person. If several preferred numerical ranges are stated in this form, of course, all the ranges formed by a combination of the different end points are also included.

The terms "about" or "approximately" or "around" as used herein when referring to a measurable value such as a parameter, an amount, a temporal duration, and the like, are meant to encompass variations of and from the specified value, such as variations of +/−5% or less, +/−1% or less, and +/−0.1% or less of and from the specified value, insofar such variations are appropriate to perform in the disclosed invention. It is to be understood that the value to which the modifier "about" or "approximately" or "around" refers is itself also specifically, and preferably, disclosed.

As used herein, the terms "include" (any form of "include", such as "include"), "have" (and "have"), "comprise" etc. any form of "having", "including" (and any form of "including" such as "including"), "containing", "comprising" or "comprises" are inclusive and will be understood to imply the inclusion of a stated element, integer or step, or group of elements, integers or steps, but not the exclusion of any other element, integer or step, or group of elements, integers or steps.

As regards the embodiments characterized in this specification, it is intended that each embodiment be read independently as well as in combination with another embodiment. For example, in case of an embodiment 1 reciting 3 alternatives A, B and C, an embodiment 2 reciting 3 alternatives D, E and F and an embodiment 3 reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Any discussion of documents, acts, materials, devices, articles and the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

We claim:

1. A method of reducing or eliminating microbes from a solid surface comprising:
    coating the solid surface with a quaternary ammonium compound at a temperature of 25° C. to 100° C. for 2-10 hours to obtain a coated solid surface; and
    applying an electric field to the coated solid surface using an electrical power source, wherein the applied electric field has an intensity of 2 kilovolts per centimeter (kV/cm) to 6 kilovolts per centimeter (kV/cm); and wherein the electrical power source is coupled with a capacitor that provides a capacitance of 0.002 microfarads (µF) to 0.06 microfarads (µF), to reduce or eliminate the microbes from the solid surface.

2. The method as claimed in claim 1, wherein the electric field is applied to the coated solid surface after contamination with the microbes.

3. The method as claimed in claim 1, wherein the quaternary ammonium compound is a quaternary ammonium salt, wherein the quaternary ammonium salt is a linear alkyl quaternary ammonium salt having aliphatic carbon chain length of C8 to C22.

4. The method as claimed in claim 3, wherein the quaternary ammonium salt is a linear alkyl quaternary ammonium salt having aliphatic carbon chain length of C16 to C18;

wherein the linear alkyl quaternary ammonium salt having aliphatic carbon chain length of C16 to C18 is a cetrimonium salt or a steartrimonium salt;

or wherein the linear alkyl quaternary ammonium salt having aliphatic carbon chain length of C16 to C18 is selected from a group comprising cetyltrimethylammonium bromide (CTAB), cetyltrimethylammonium chloride (CTAC), stearyl trimethyl ammonium chloride (STAC) and mixtures thereof.

5. The method as claimed in claim 1, wherein the quaternary ammonium compound is cetyltrimethylammonium bromide (CTAB).

6. The method as claimed in claim 1, wherein the solid surface is coated with about 0.01% (w/v) to 1% (w/v) of the quaternary ammonium compound;

or the solid surface is coated with about 0.01 to 0.05 milligram (mg) of the quaternary ammonium compound per square centimeter ($cm^2$) of said solid surface.

7. The method as claimed in claim 1, wherein the quaternary ammonium compound coated on the solid surface has a thickness of about 0.1 to 3 millimeter (mm).

8. The method as claimed in claim 1, wherein the intensity of the applied electric field is 2 kV/cm to 4 kV/cm and the capacitance provided by the capacitor is 0.0025 μF to 0.05 μF.

9. The method as claimed in claim 1, wherein the electrical power source is selected from a group comprising direct current (DC) power source, alternating current (AC) power source, switch mode power supply (SMPS) source, or pulsed power source.

10. The method as claimed in claim 1, wherein the coated solid surface is subjected to electric field for a time-period of about 3 minutes to 90 minutes, or about 10 minutes to 60 minutes.

11. The method as claimed in claim 1, wherein the solid surface is selected from a group comprising fabric, fibre, metal, wood, plastic, glass, polymer, and combinations thereof.

12. The method as claimed in claim 1, wherein the microbes are selected from a group comprising bacteria, virus, fungus, microbial spores, and combinations thereof.

13. The method as claimed in claim 1, wherein said method achieves a microbial load reduction of about 4 $log_{10}$ to 7 $log_{10}$; or said method reduces microbial load on the solid surface by about 95% to 99.9999%.

14. The method as claimed in claim 1, wherein:

the quaternary ammonium compound is linear alkyl quaternary ammonium salt having aliphatic carbon chain length of C8 to C22, linear alkyl quaternary ammonium salt having aliphatic carbon chain length of C16 to C18, or CTAB;

the solid surface is fabric, metal or polymer; and the intensity of the applied electric field is 2 kV/cm to 4 kV/cm and the capacitance provided by the capacitor is 0.0025 μF to 0.05 μF, to reduce or eliminate the microbes from the solid surface.

15. A kit comprising:

a quaternary ammonium compound, or a solid material coated with the quaternary ammonium compound, wherein the solid material is coated with the quaternary ammonium compound at a temperature of 25° C. to 100° C. for 2-10 hours;

an electrical power source to supply an electric field, wherein the electric field supplied by the electrical power supply has an intensity of 2 kV/cm to 6 kV/cm;

and wherein the electrical power supply is coupled with a capacitor that provides a capacitance of 0.002 μF to 0.06 μF; and an instruction manual comprising instructions for reducing or eliminating microbes from a solid surface.

16. A solid material or a device comprising:

a coating of quaternary ammonium compound, wherein the coating is applied to the solid material or device at a temperature of 25° C. to 100° C. for 2-10 hours; and an electric filled is applied to the solid material or device using an electrical power source, wherein the applied electric field has an intensity of 2 kV/cm to 6 kV/cm; and wherein the electrical power supply is coupled with a capacity that provides a capacitance of 0.002 μF to 0.06 μF.

17. The kit as claimed in claim 15, wherein the quaternary ammonium compound is a quaternary ammonium salt, wherein said quaternary ammonium salt is a linear alkyl quaternary ammonium salt having aliphatic carbon chain length of C16 to C18 selected from a group comprising cetyltrimethylammonium bromide (CTAB), cetyltrimethylammonium chloride (CTAC), stearyl trimethyl ammonium chloride (STAC), and mixtures thereof;

wherein the electrical power source supplies an electric field having an intensity of 2 kV/cm to 4 kV/cm; and wherein the electrical power source is coupled to a capacitor that provides a capacitance of 0.0025 μF to 0.05 μF;

and wherein the solid material is a medical device, or an industrial device.

18. The solid material or the device as claimed in claim 16, wherein the quaternary ammonium compound is a quaternary ammonium salt, wherein said quaternary ammonium salt is a linear alkyl quaternary ammonium salt having aliphatic carbon chain length of C16 to C18 selected from a group comprising cetyltrimethylammonium bromide (CTAB), cetyltrimethylammonium chloride (CTAC), stearyl trimethyl ammonium chloride (STAC), and mixtures thereof;

wherein the intensity of the applied electric field is 2 kV/cm to 4 kV/cm and the capacitance provided by the capacity is 0.0025 μF to 0.05 μF;

and wherein the solid material is a medical device, or an industrial device.

* * * * *